United States Patent [19]

Ohfune et al.

[11] Patent Number: 4,837,349
[45] Date of Patent: Jun. 6, 1989

[54] TERTIARY-BUTYLDIMETHYLSILYL CARBAMATE DERIVATIVE AND PROCESS FOR PRODUCING THE SAME

[75] Inventors: Yasufumi Ohfune; Masahiro Sakaitani, both of Osaka, Japan

[73] Assignee: Suntory Limited, Osaka, Japan

[21] Appl. No.: 909,397

[22] Filed: Sep. 19, 1986

[30] Foreign Application Priority Data

Sep. 19, 1985 [JP] Japan .................. 60-207204
Jul. 11, 1986 [JP] Japan .................. 61-163443

[51] Int. Cl.$^4$ .............................................. C07F 7/10
[52] U.S. Cl. .................................... 556/420; 548/110; 549/214
[58] Field of Search ..................... 556/420; 548/110; 549/214

[56] References Cited

U.S. PATENT DOCUMENTS

| | | | |
|---|---|---|---|
| 4,400,526 | 8/1983 | Kanner et al. | 556/420 |
| 4,496,754 | 1/1985 | Kanner et al. | 556/420 |
| 4,631,346 | 12/1986 | Webb et al. | 556/420 |

FOREIGN PATENT DOCUMENTS

| | | | |
|---|---|---|---|
| 0114399 | 12/1983 | European Pat. Off. | 556/420 U X |
| 0540869 | 12/1976 | U.S.S.R. | 556/420 |

OTHER PUBLICATIONS

Journal of Pharmaceutical Sciences, vol. 71, No. 5, May 1982, pp. 542–551 "Synthesis, Hydrolytic Reactivity . . ."

Green, "Protective Groups in Organic Synthesis", p. 232.

J. Am. Chem. Soc., 72, 725 (1950) "Carboallyloxy Derivatives of a-Amino Acids" by Carl M. Stevens & Ronald Wantanabe.

Tetrahedron Letters, vol. 26, No. 27, pp. 3223–3226, 1985, New Methods and Reagents in Organic Synthesis 51+,1, A Synthesis of Ascidiacyclamide, A cytotoxic Cyclic Peptide from Ascidan. . .

"Angewandte Chemie International Edition" 14, 818 (1975).

Primary Examiner—Paul F. Shaver
Attorney, Agent, or Firm—Cushman, Darby & Cushman

[57] ABSTRACT

A t-butyldimethylsilyl carbamate derivative and a process for producing the same are disclosed. Tertiary-butyldimethylsilyl carbamate derivatives having the following general formula (1) are intermediates for the production of a variety of carbamate esters that can be extensively used as drugs acting on the central nervous system or circulatory organs, as agrichemicals (e.g. insecticides and herbicides), or as antimicrobial agents; a process capable of economical and efficient production of such intermediates is also disclosed:

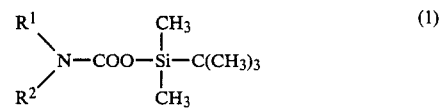

(1)

where $R^1$ is an alkyl group having 1–3 carbon atoms or a hydrogen atom; $R^2$ is

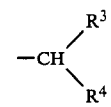

(where $R^3$ is a hydrogen atom, an alkyl, alkenyl or aralkyl group having 1–10 carbon atoms, each of which groups may be substituted by a hydroxyl group, a t-butyldimethylsilyloxy group, a methylthio group, a lower alkoxycarbonyl group, a lower alkoxy group, an indolyl group or an imidazolyl group; $R^4$ is a lower alkoxycarbonyl group, an N-alkylamido group having 2–6 carbon atoms, an O-tetrahydropyranylthreonine methyl ester amido residue, an O-t-butyldimethylsilyl-threonine methyl ester amido residue, a threonine methyl ester amido residue or —$(CH_2)_n$—$COOR^5$ (where n is an integer of 1–3 and $R^5$ is a lower alkyl group), provided that $R^3$ combines with $R^4$ to form a cyclopentyl group, a cyclohexyl group, a tetrahydrofuranyl group or a dioxanyl group, these rings being optionally substituted by a lower alkyl group, a lower alkenyl group, a lower alkoxycarbonyl group or a lower alkoxycarbonylmethyl group); and $R^1$ and $R^2$, when taken together, form a 4- or 5-membered carbon ring, which may be substituted by a lower alkoxycarbonyl group or a t-butyldimethylsilyloxycarbonyl group.

3 Claims, No Drawings

TERTIARY-BUTYLDIMETHYLSILYL CARBAMATE DERIVATIVE AND PROCESS FOR PRODUCING THE SAME

The present invention relates to a t-butyldimethylsilyl carbamate derivative of the general formula (1):

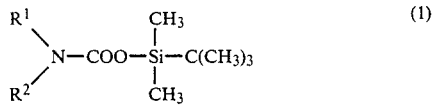

where $R^1$ is an alkyl group having 1–3 carbon atoms or a hydrogen atom; $R^2$ is

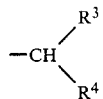

(where $R^3$ is a hydrogen atom, an alkyl, alkenyl or aralkyl group having 1–10 carbon atoms, each of which groups may be substituted by a hydroxyl group, a t-butyldimethylsilyloxy group, a methylthio group, a lower alkoxycarbonyl group, a lower alkoxy group, an indolyl group or a imidazolyl group; $R^4$ is a lower alkoxycarbonyl group, an N-alkylamido group having 2–6 carbon atoms, an O-tetrahydropyranylthreonine methyl ester amido residue, an O-t-butyldimethylsilylthreonine methyl ester amido residue, a threonine methyl ester amido residue, or $-(CH_2)_n-COOR^5$ (where n is an integer of 1–3 and $R^5$ is a lower alkyl group), provided that $R^3$ combines with $R^4$ to form a cyclopentyl group, a cyclohexyl group, a tetrahydrofuranyl group or a dioxanyl group, these rings being optionally substituted by a lower alkyl group, a lower alkenyl group, a lower alkoxycarbonyl group or a lower alkoxycarbonylmethyl group); and $R^1$ and $R^2$, when taken together, form a 4- or 5-membered carbon ring, which may be substituted by a lower alkoxycarbonyl group or a t-butyldimentylsilyloxycarbonyl group. The present invention also relates to a process for producing said carbamate derivative.

The compounds of formula (1) produced by the method of the present invention can be readily reacted with halides to form a variety of carbamate esters. The produced carbamate esters are compounds that are useful not only as pharmaceuticals acting on the central nervous system or the circulatory organs but also as agriculturalchemicals (e.g. insecticides, acaricides and herbicides) and as antimicrobial agents.

Tertiary-butoxycarbonyl group (Boc group), benzyloxycarbonyl group (Z group) and allyloxycarbonyl group (Alloc group) are typical urethane-type amino protecting groups and have been extensively used in the synthesis of amino acids, amino sugars, nucleic acids and peptides, as detailed in Protective Group in Organic Synthesis, John Wiley & Sons, New York, p. 232, 1981. These useful protective groups have the following chemical properties:

(1) Boc group

Stable under basic or reducing conditions but labile in acids, so acidic conditions are employed to remove the Boc group. However, acidic conditions cannot be used if a functional group labile under acidic conditions is present. Shioiri et al. recently solved this problem by treatment with trimethylsilyltrifluoromethane sulfonate (Tetrahedron Letters, 26, 3223, 1985);

(2) Z group

Stable under acidic conditions but labile under basic or reducing conditions and, hence, is usually removed by catalytic hydrogenation. However, this is not possible in the presence of a double band, a triple band, a benzyl group, an alkylthio group, an allylthio group or a dithio group. Birkofen et al. solved this problem by employing triethyl silane and palladium (II) chloride (Chemi. Ber., 94, 821, 1961);

(3) Alloc group

Stable under weak acidic conditions or basic conditions and cannot be removed under reducing conditions. This group is therefore removed either under strong acidic conditions or under oxidizing conditions in the presence of a metal catalyst (C. M. Stevens, Journal of American Chemical Society, 72, 725, 1950).

However, no case has been reported of success in isolating as a stable compound the N-carboxylate ion ($N-CO_2^-$) produced as an intermediate under the removal conditions described in (1) to (3), to say nothing of the accomplishment of various chemical transformations as accompanied by conversion of one protective group to another (e.g. Boc group→Z group).

The present inventors made concerted efforts to devise a method for achieving ready conversion of an amino-protecting group during peptide synthesis. Since carbamate ester groups typified by Boc and Z groups are useful functional groups in medical and agrichemical fields, the present inventors also conducted studies in order to develop a new method of synthesis capable of converting these functional groups directly to a variety of cabamate esters after they have been used as amino-protective groups.

In the removal of Boc group using trimethylsilyltrifluoromethane sulfonate, the trimethylsilylcarbamate ester group which can be regarded as an intermediate is labile and defines isolation. In the reaction system employing triethylsilane and palladium (II) acetate, the resulting triethylsilyl carbamate cannot be isolated because of the alcoholic solvent used for post-treatment of the reaction. These would be the principal reasons why conversion of Boc and Z groups has been impossible in the prior art.

The t-butyldimethylsilyl cabamate derivative of the present invention having the general formula (1) can be prepared by one of the following methods (A) and (B):

(A) A t-butoxycarbonylated amino group having the following formula (2) is reacted with t-butyldimethylsilyltrifluoromethane sulfonate (TBDMSOTf):

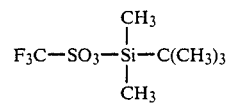

in an organic solvent in the presence of a base:

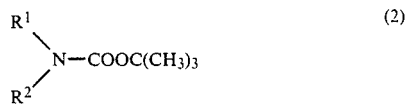

where $R^1$ is an alkyl group having 1–3 carbon atoms or a hydrogen atom; $R^2$ is

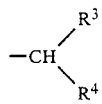

(where R³ is a hydrogen atom, an alkyl, alkenyl or aralkyl group having 1-10 carbon atoms, each of which groups may be substituted by a hydroxyl group, a t-butyldimethylsilyloxy group, a methylthio group, a lower alkoxycarbonyl group, a lower alkoxy group, an indolyl group or an imidazolyl group; R⁴ is a lower alkoxycarbonyl group, an N-alkylamido group having 2-6 carbon atoms, an O-tetrahydropyranylthreonine methyl ester amido residue, an O-t-butyldimethylsilyl-threonine methyl ester amido residue, a threonine methyl ester amido residue, or —(CH₂)ₙ—COOR⁵ (where n is an integer of 1-3 and R⁵ is a lower alkyl group), provided that R³ combines with R⁴ to form a cyclopentyl group, a cyclohexyl group, a tetrahydurfuranyl group or a dioxanyl group, these rings being optionally substituted by a lower alkyl group, a lower alkenyl group, a lower alkoxycarbonyl group or a lower alkoxycarbonylmethyl group); and R¹ and R², when taken together, form a 4- or 5-membered carbon ring, which may be substituted by a lower alkoxycarbonyl group.

Because of the instability of the reactants employed, the reaction described above must be carried out in an anhydrous organic solvent, with an anhydrous chlorine-based solvent being particularly preferable.

Typical examples of the base include: pyridines such as lutidine, N-dimethylaminopyridine, methylpyridine and pyridine; and trialkylamines such as triethylamine, diisopropylmethylamine, diisopropylethylamine, dibutylmethylamine and triisopropylamine.

The reaction is generally carried out at room temperature or below, preferably at a temperature within the range of from −10° to 25° C.

(B) A benzyloxycarbonylated or allyloxycarbonylated amino group having the general formula (3):

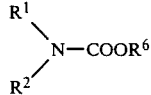

(3)

(where R¹ and R² are the same as defined above; R⁶ is a benzyl group or an allyl group) is reacted with t-butyldimethylsilane of the formula:

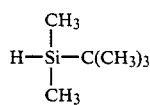

in an organic solvent in the presence of a palladium catalyst.

Because of the instability of the reactants employed, the reaction described above must also be carried out in an anhydrous organic solvent, with an anhydrous chlorine-based solvent being particularly preferable.

Typical examples of the palladium catalyst include palladium on carbon, palladium (II) chloride, palladium (II) acetate, dichlorobis(acetonitrile) palladium (II), and dichlorobis(triphenylphosphine) palladium (II).

The reaction is generally carried at room temperature or below, with the range of from −10° to 25° C. being preferable.

In applications of the methods (A) and (B), Boc or Z group (or Alloc group) may be selectively converted to the t-butyldimethylsilyloxycarbonyl group, as illustrated below.

(1)

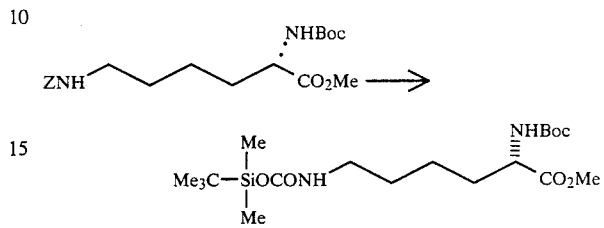

To a dichloromethane solution (1.0 ml) of palladium (II) acetate (6 mg, 0.03 mmol) and triethylamine (12 μl, 0.09 mmol) were successively added t-butyldimethylsilane (63 μl, 0.38 mmol) and a dichloromethane solution (1.0 ml) of Nα-t-butoxycarbonyl-Nε-benzyloxycarbonyllysine methyl ester (100 mg, 0.25 mmol). The mixture was stirred for 16 hours in an argon atmosphere at room temperature. After addition of a saturated aqueous solution of ammonium chloride, the reaction mixture was extracted with ether. The ether layer was dried over anhydrous magnesium sulfate, filtered and distilled to remove the solvent, thereby yielding Nα-butoxycarbonyl-Nε-t-butyldimethylsilyloxycarbonyllysine methyl ester (95.5 mg; yield, 90%).

Appearance: colorless oil.

IR spectrum (film, cm⁻¹): 3368, 1748, 1704, 1520.

Mass spectrum (m/z): 419 (M⁺ +1)⁺, 345, 305, 287.

NMR spectrum (CDCl₃, δ ppm): 5.00(2H, m), 4.20(1H, m), 3.69(3H, s), 3.08(2H, m), 1.42(9H, s), 1.1-2.0(6H, m), 0.91(9H, s), 0.24(6H, s).

(2)

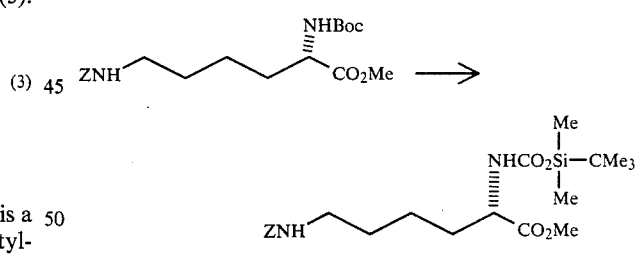

To a dichloromethane solution (1.0 ml) of Nα-t-butoxycarbonyl-Nε-benzyloxycarbonyllysine methyl ester (191.0 mg, 0.48 mmol) were added 2.6-lutidine (113 μl, 0.97 mmol) and t-butyldimethylsilyltrifluoromethane sulfonate (167 μl, 0.73 mmol). The mixture was stirred for 15 minutes in an argon atmosphere at room temperature. After addition of a saturated aqueous solution of ammonium chloride, the reaction mixture was extracted with ether and the ether layer was dried over anhydrous magnesium sulfate and filtered. After removal of the solvent in vacuo, Nα-butyldimethylsilyloxycarbonyl-Nε-benzyloxycarbonyllysine methyl ester was obtained (238 mg; yield, 100%).

Appearance: colorless oil.

IR spectrum (film, cm⁻¹): 3352, 1708, 1526.

Mass spectrum (m/z): 452 M⁺, 395, 352.

NMR spectrum (CDCl$_3$, δ ppm): 7.35(5H, s), 5.24(1H, d, J=8.0 Hz), 5.09(2H, s), 4.80(1H, brs), 4.15(1H, m), 3.74(3H, s), 3.19(2H, m), 1.2–1.9(6H, m), 0.94(9H, s).

Surprisingly enough, the compounds of the present invention thus prepared can react with a variety of halides to form carbamate esters. For instance, if the t-butyldimethylsilyl carbamate derivative of formula (1) is reacted with a benzyl halide at room temperature or below, preferably at between −10° and 25° C., in the presence of a tetraalkylammonium fluoride, a compound represented by the following general formula (4) wherein the amino group is protected with a benzyloxycarbonyl group (Z group) is readily obtained:

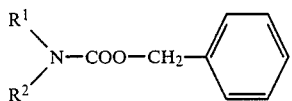  (4)

where R$^1$ and R$^2$ are the same as defined above.

In this manner, the amino-protecting group such as Boc group can be converted from Boc to Z. By repeating the same method except that the benzyl halide is replaced by an alkyl halide and an aryl halide, carbamate esters having the following general formulas (5) and (6), respectively, can be attained:

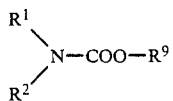  (5)

(where R$^9$ is an alkyl group); and

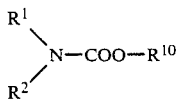  (6)

(where R$^{10}$ is an aryl group).

By employing the methods described above, medicines and agrichemicals can be synthesized as illustrated below:

(1) Diperodon (local anesthetic):

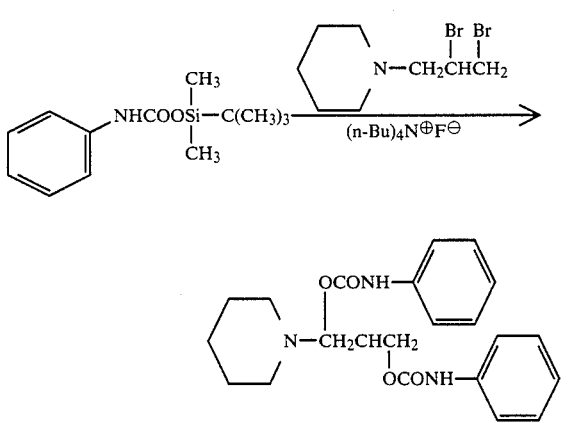

(2) Hexacarbacholine bromide (skeletal muscle relaxant):

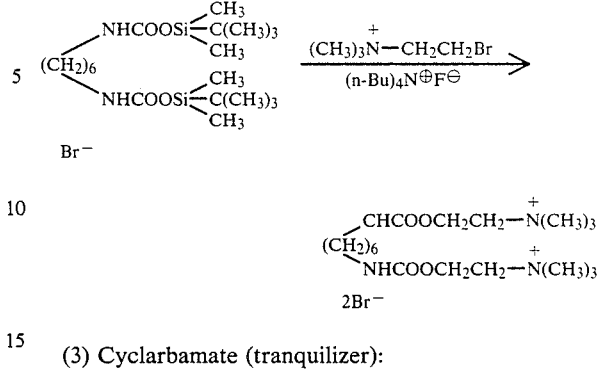

(3) Cyclarbamate (tranquilizer):

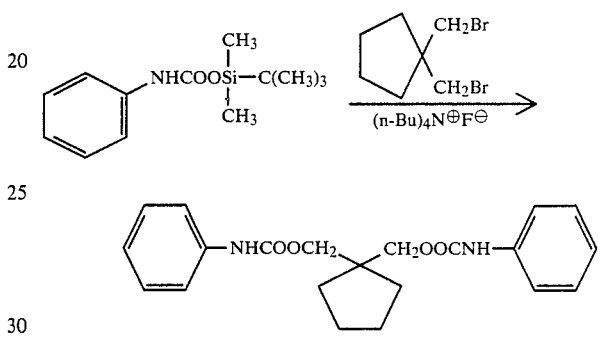

(4) Ecarazine hydrochloride:

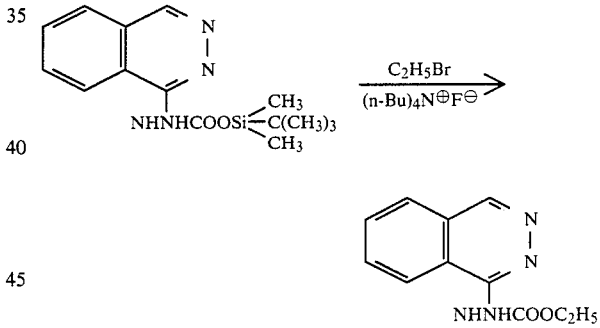

(5) Thymyl N-isoamylcarbamate (insecticide):

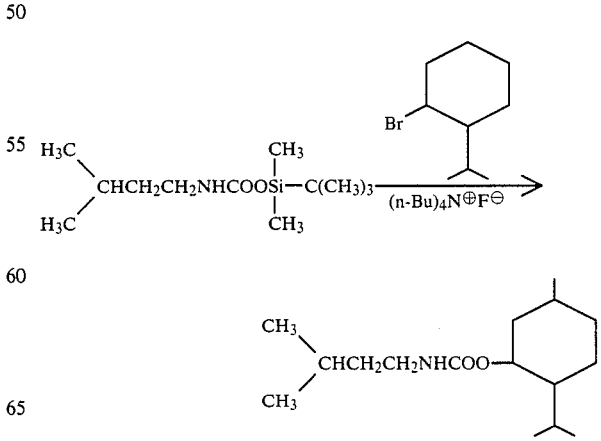

(6) Propamocarb hydrochloride (fungicide)

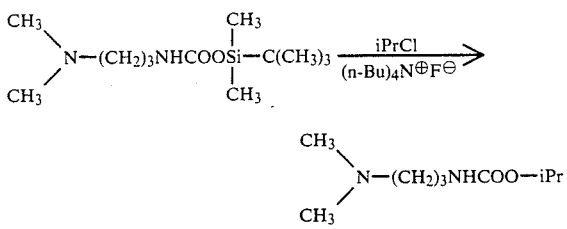

(7) Tolnaftate (antimicrobial agent):

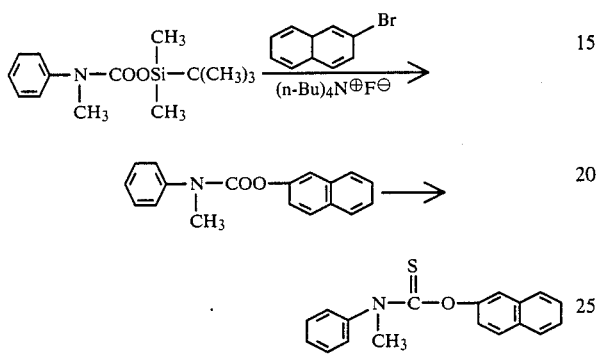

In the reaction schemes shown above, n-Bu signifies an n-butyl group.

The essence of the present invention lies in obtaining the t-butyldimethylsilyl carbamate of formula (1) either by treating the N-Boc group with t-butyldimethylsilyl trifluoromethan sulfonate or by treating the N-Z group or N-Alloc group with t-butyldimethylsilane in the presence of a palladium (II) catalyst. As previously mentioned, trimethylsilyl carbamate can be derived either from the N-Boc group by treatment with trimethylsilyl trifluoromethan sulfonate or from the N-Z group or N-Alloc group by treatment with trimethylsilane in the presence of a palladium (II) catalyst. However, the thus obtained trimethylsilyl carbamate is too labile to be suitable for achieving the conversion intended by the present invention. It would be an obvious matter for those skilled in the art to realize that in achieving conversion from the Boc group, t-butyldimethylsilyl trifluoromethan sulfonate may be replaced by, for example, dimethylphenylsilyl triflruoromethan sulfonate and triethylsilyl trifluoromethan sulfonate to obtain dimethylphenylsilyl carbamate and triethylsilyl carbamate, respectively. It would also be obvious for those skilled in the art to obtain dimethylphenylsilyl carbamate and triethylsilyl carbamate from the Z or Alloc group by treatment with dimethylphenylsilane and triethylsilane, respectively, in the presence of a palladium (II) catalyst.

The dimethylphenylsilyl or triethylsilyl carbamate thus prepared may be reacted with a halide in the presence of a tetraalkyl ammonium fluoride so as to attain a carbamate ester having a variety of corresponding trisubstituted groups.

The t-butyldimethylsilyl carbamate derivatives of the present invention generally are not highly stable but side reactions are not likely to occur during their syntheses because the reaction conditions employed are very mild.

As will be shown in the Examples given below, even if optically active amino acid derivatives are used as starting materials, any racemination cannot be detected during preparation of the t-butyldimethylsilyl carbamate and conversion into its carbamate esters.

The compounds of the present invention are very active and are desirably subjected to subsequent reactions immediately after their synthesis.

The following examples are provided for the purpose of further illustrating the syntheses of the compounds of the present invention but are in no way to be taken as limiting. Methods of producing carbamate esters from the compounds of the present invention are also shown in the Reference Examples.

EXAMPLE 1

N-(t-Butyldimethylsilyloxycarbonyl)-2-amino-4-pentenoyl-O-(t-butyldimethylsilyl)-threonine methyl ester

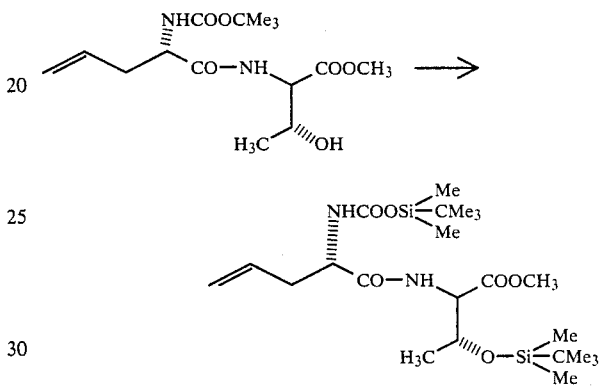

(Me=methyl; this definition will apply in the other formulas)

To a methylene chloride solution (1.0 ml) of N-(t-butoxycarbonyl)-2-amino-4-pentenoyl-threonine methyl ester (24 mg, 0.07 mmol) and 2,6-lutidine (0.024 ml, 0.21 mmol) was added dropwise t-butyldimethyl-silyltrifluoromethane sulfonate (TBDMSOTf) (0.041 ml, 0.18 mmol) at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent under vacuum, the titled compound was obtained in an amount of 43.3 mg.

Appearance: colorless oil.

Mass spectrum (m/z): 458 (M-44)+, 445 (M-t-Bu)+, 313.

NMR spectrum (CDCl$_3$, δ): −0.03(3H, s), 0.04(3H, s), 0.24(3H, s), 0.25(3H, s), 0.84(9H, s), 0.90(9H, s), 1.14(3H, d, J=7.0 Hz), 2.54(2H, m), 3.69(3H, s), 4.0–6.0(7H, m), 6.52(1H, d, J=8.0 Hz).

EXAMPLE 2

N-(t-Butyldimethylsilyloxycarbonyl)-2-amino-4-pentenoyl-O-(tetrahydropyranyl)-threonine methyl ester

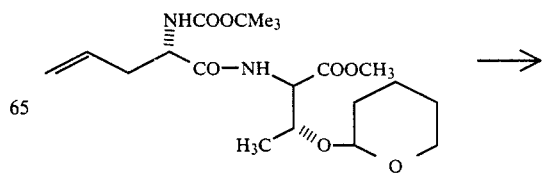

-continued

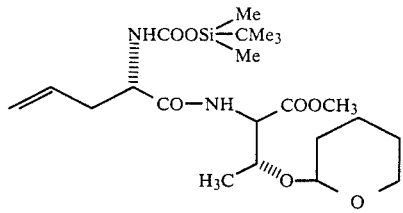

To a methylene chloride solution (1.0 ml) of N-(t-butoxycarbonyl)-2-amino-4-pentenoyl-O-(tetrahydropyranyl)threonine methyl ester (37 mg, 0.09 mmol) and 2,6-lutidine (0.021 ml, 0.18 mmol) was added dropwise t-butyldimethylsilyltrifluoromethane sulfonate (TBDMSOTf) (0.031 ml, 0.14 mmol) at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent under vacuum, the titled compound was obtained in an amount of 45.8 mg.

Appearance: colorless oil.

Mass spectrum (m/z) 472 (M)+, 415.

NMR spectrum (CDCl₃, δ): 0.25(6H, s), 0.90(9H, s), 1.55(6H, brs), 2.50(2H, m), 3.67(3H, s).

EXAMPLE 3

Methyl N-(t-butyldimethylsilyloxycarbonyl)-2-amino-4-pentenoate

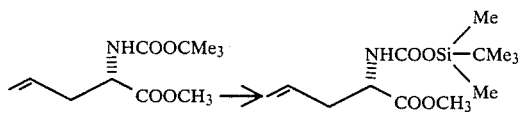

To a methylene chloride solution (1.5 ml) of N-(t-butoxycarbonyl)-allylglycine methyl ester (183 mg, 0.8 mmol) and 2,6-lutidine (0.186 ml, 1.6 mmol) was added t-butyldimethylsilyltrifluoromethane sulfonate (TBDMSOTf) (0.275 ml, 1.2 mmol) at room temperature in a nitrogen atmosphere. After the mixture was stirred for 15 minutes, a saturated aqueous solution of ammonium chloride (3 ml) was added to quench the reaction and extraction with ether was conducted. The organic layer was dried over anhydrous magnesium sulfate and filtered. By distilling off the solvent under vacuum, the titled compound was obtained in an amount of 260 mg.

Appearance: colorless oil.

IR spectrum (film, cm⁻¹): 3372, 3100, 1760, 1710.

Mass spectrum (m/z): 288 (M+1)+.

NMR spectrum (CDCl₃, δ): 0.25(6H, s), 0.92(9H, s), 2.52(2H, m), 3.73(3H, s), 4.40(1H, dt, J=8, 6 Hz), 4.9–5.3(3H, m), 5.70(1H, ddt, J=18, 10, 6 Hz).

EXAMPLE 4

N-(t-Butyldimethylsilyloxycarbonyl)-valine methyl ester

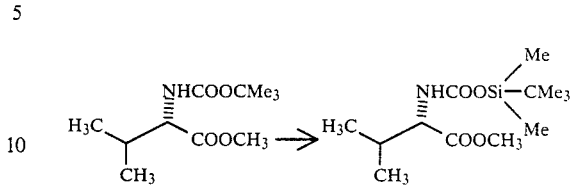

To a methylene chloride solution (1.0 ml) of N-t-butoxycarbonyl-L-valine methyl ester (115.5 mg, 0.5 mmol) and 2,6-lutidine (0.116 ml, 1.0 mmol) was added dropwise t-butyldimethylsilyltrifluoromethane sulfonate (0.172 ml, 0.75 mmol) at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent under vacuum, the titled compound was obtained in an amount of 153.2 mg.

Appearance: colorless oil.

IR spectrum (film, cm⁻¹): 3380, 1748, 1716, 1506.

Mass spectrum (m/z): 290 (M+1)+, 274, 232, 160.

NMR spectrum (CDCl₃, δ): 0.26(6H, s), 0.94(9H, s), 0.92(3H, d, J=7.0 Hz), 0.98(3H, d, J=7.0 Hz), 2.15(1H, m), 3.72(3H, s), 4.20(1H, dd, J=10, 5 Hz), 5.28(1H, d, J=10 Hz).

EXAMPLE 5

N-(t-Butyldimethylsilyloxycarbonyl)-L-methionine methyl ester

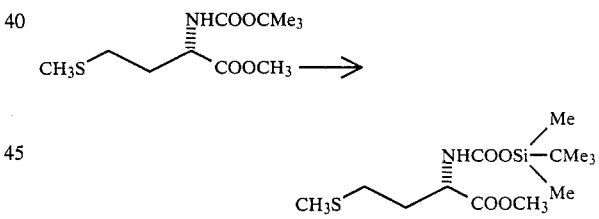

To a methylene chloride solution (1.0 ml) of N-t-butoxycarbonyl-L-methionine methyl ester (131.5 mg, 0.5 mmol) and 2,6-lutidine (0.116 ml, 1.0 mmol), t-butyldimethylsilyltrifluoromethane sulfonate (TBDMSOTf) (0.172 ml, 0.75 mmol) was added dropwise at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent under vacuum, the titled compound was obtained in an amount of 146 mg.

Appearance: colorless oil.

IR spectrum (film, cm⁻¹): 3368, 1748, 1704, 1516.

Mass spectrum (m/z): 321 (M)+, 264, 220.

NMR spectrum (CDCl₃, δ): 0.25(6H, s), 0.92(9H, s), 2.09(3H, s), 1.8–2.7(4H, m), 3.72(3H, s), 4.38(1H, dt, J=8, 7 Hz), 5.45(1H, d, J=8 Hz).

EXAMPLE 6

N-(t-Butyldimethylsilyloxycarbonyl)-phenylalanine methyl ester

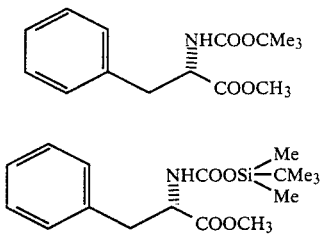

To a methylene chloride solution (1.0 ml) of N-t-butoxycarbonyl-L-phenylalanine methyl ester (139.5 mg, 0.5 mmol) and 2,6-lutidine (0.116 ml, 1.0 mmol), t-butyldimethylsilyltrifluoromethane sulfonate (TBDMSOTf) (0.172 ml, 0.75 mmol) was added dropwise at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent, the titled compound was obtained in an amount of 186.8 mg.

Appearance: colorless oil.

Mass spectrum (m/z): 322 (M-15)+, 208.

NMR spectrum (CDCl$_3$, δ): 0.25(6H, s), 0.92(9H, s), 3.05(2H, d, J=6.0 Hz), 3.65(3H, s), 4.55(1H, dt, J=9.0, 6.0 Hz), 5.22(1Hd, d, J=9.0 Hz), 7.17(5H, m).

EXAMPLE 7

N-(t-Butyldimethylsilyloxycarbonyl)-proline methyl ester

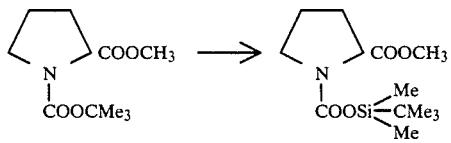

To a methylene chloride solution (1 ml) of N-t-butoxycarbonyl-L-proline methyl ester (114.5 mg, 0.5 mmol) and 2,6-lutidine (0.116 ml, 1.0 mmol), t-butyldimethylsilyltrifluoromethane sulfonate (TBDMSOTf) (0.172 ml, 0.75 mmol) was added dropwise at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent under vacuum, the titled compound was obtained in an amount of 153 mg.

Appearance: colorless oil.

IR spectrum (film, cm$^{-1}$): 3350, 1660.

Mass spectrum (m/z): 272 (M-15)+, 243, 231.

NMR spectrum (CDCl$_3$, δ): 0.25(6H, s), 0.86, 0.92(9H in all, s each), 1.7-2.4(4H, m), 3.47(2H, t, J=6 Hz), 3.65, 3.68(3H in all, s each), 4.25(1H, m).

EXAMPLE 8 t-Butyl(4S*, 5R*,6R*)-N-(t-butyldimethylsilyloxycarbonyl)5-amino-2,2-dimethyl-6-vinyl-1,3-dioxane-4-acetate

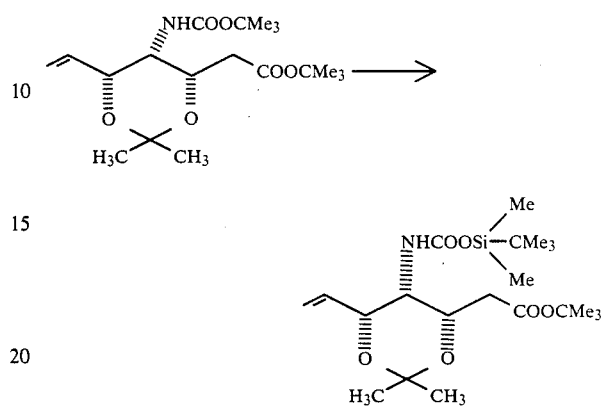

To a methylene chloride solution (0.5 ml) of t-butyl(4S*,5R*,6R*)-N-benzyloxycarbonyl-5-amino-2,2-dimethyl-6-vinyl-1,3-dioxane-4-acetate (41 mg, 0.11 mmol) and 2,6-lutidine (0.026 ml, 0.22 mmol), t-butyldimethylsilyltrifluoromethane sulfonate (TBDMSOTf) (0.038 ml, 0.16 mmol) was added dropwise at room temperature in a nitrogen atmosphere. After the mixture was stirred for 15 minutes, a saturated aqueous solution of ammonium chloride (2 ml) was added to quench the reaction and extraction with ether was conducted. The organic layer was dried over anhydrous magnesium sulfate and filtered. By distilling off the solvent under vacuum, the titled compound was obtained in an amount of 46 mg.

Appearance: colorless oil.

IR spectrum (film, cm$^{-1}$): 1734, 1718.

Mass spectrum (m/z): 430 (M+1)+, 414, 358.

NMR spectrum (CDCl$_3$, δ): 0.25(6H, s), 0.93(9H, s), 1.45(12H, s), 1.50(3H, s), 2.40(2H, d, J=6 Hz), 3.60(1H, d, J=9 Hz), 4.45(2H, m), 4.9-6.1(4H, m).

EXAMPLE 9

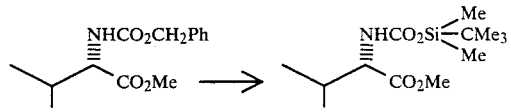

To a dichloromethane solution (1.0 ml) of palladium (II) acetate (13 mg, 0.06 mmol) and triethylamine (25 μl, 0.18 mmol), t-butyldimethylsilane (282 μl, 1.7 mmol) was added and the mixture was stirred for 15 minutes at room temperature in an argon atmosphere. To the resulting black suspension, a dichloromethane solution (1.0 ml) of Z valine methyl ester (300 mg, 1.1 mmol) was added and the mixture was stirred for an additional 16 hours. After a saturated aqueous solution of ammonium chloride was added to quench the reaction, extraction with ether was conducted. The ether layer was dried over anhydrous magnesium sulfate and filtered. By distilling off the solvent, N-t-butyldimethylsilyloxycarbonylvaline methyl ester was obtained in an amount of 327 mg (yield, 100%). All the data for this compound were in agreement with those reported in Example 4.

EXAMPLE 10

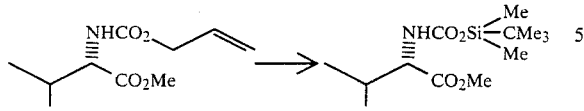

To a dichloromethane solution (1.0 ml) of palladium (II) acetate (8.0 mg, 0.04 mmol) and triethylamine (15 μl, 0.11 mmol), t-butyldimethylsilane (179 μl, 1.1 mmol) was added and the mixture was stirred for 15 minutes at room temperature. To the resulting black suspension, a dichloromethane solution (1.0 ml) of N-allyloxycarbonylvaline methyl ester (154 mg, 0.72 mmol) was added and the mixture was stirred for an additional 15 hours. After a saturated aqueous solution of ammonium chloride was added to quench the reaction, extraction with ether was conducted and the ether layer was dried over anhydrous magnesium sulfate and filtered. By distilling off the solvent, N-t-butyldimethylsilyloxycarbonylvaline methyl ester was obtained in an amount of 207 mg (yield, 100%). The physical data for this compound were in agreement with those reported in Examples 4 and 9.

EXAMPLE 11

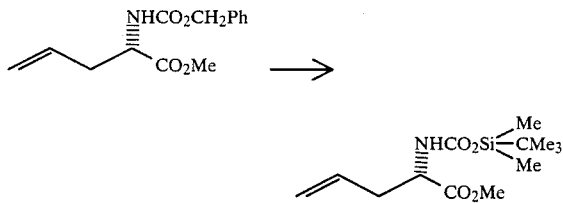

To a dichloromethane solution (1.0 ml) of palladium (II) acetate (8.0 mg, 0.04 mmol) and triethylamine (15 μl, 0.11 mmol), t-butyldimethylsilane (182 μl, 1.1 mmol) was added and the mixture was stirred for 15 minutes at room temperature in an argon atmosphere. To the resulting black suspension, a dichloromethane solution (1.0 ml) of Z-allylglycine methyl ester (192 mg, 0.73 mmol) was added and the mixture was stirred for an additional 15 hours. After a saturated aqueous solution of ammonium chloride was added to quench the reaction, extraction with ether was conducted and the ether layer was dried over anhydrous magnesium sulfate and filtered. By distilling off the solvent, a colorless oil was obtained in an amount of 204.0 mg. Analysis by $^1$H-nmr showed that this compound was a mixture of Z-allylglycine methyl ester (73 mg) and N-t-butyldimethylsilyloxycarbonylallylglycine methyl ester (130 mg, 62% yield; 100% based on the recovery of starting materials). The physical data for this compound were in agreement with those reported in Example 3.

EXAMPLE 12

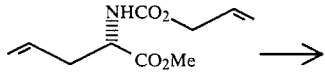

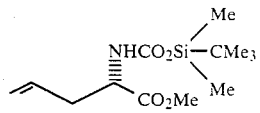

To a dichloromethane solution (1.0 ml) of palladium (II) acetate (8.0 mg, 0.04 mmol) and triethylamine (16 μl, 0.12 mmol), t-butyldimethylsilane (187 μl, 1.1 mmol) was added and the mixture was stirred for 15 minutes at room temperature in an argon atmosphere. To the resulting black suspension, a dichloromethane solution (1.0 ml) of N-allyloxycarbonylallylglycine methyl ester (150 mg, 0.75 mmol) was added and the mixture was stirred for an additional 20 hours. After a saturated aqueous solution of ammonium chloride was added to quench the reaction, extraction with ether was conducted and the ether layer was dried over anhydrous magnesium sulfate and filtered. By distilling off the solvent, N-t-butyldimethylsilyloxycarbonylallylglycine was obtained in an amount of 184 mg (yield, 90%). The physical data for this compound were in agreement with those reported in Examples 3 and 11.

EXAMPLE 13

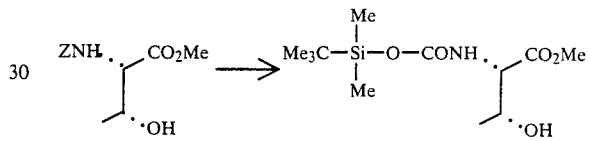

To a dichloromethane solution (1.0 ml) of palladium (II) acetate (8.0 mg, 0.04 mmol) and triethylamine (15 μl, 0.11 mmol), t-butyldimethylsilane (186 μl, 1.1 mmol) and a dichloromethane solution (1.0 ml) of Z-threonine methyl ester (200 mg, 0.75 mmol) were added successively. The mixture was stirred for 20 hours at room temperature in an argon atmosphere. After a saturated aqueous solution of ammonium chloride was added, extraction with ether was conducted and the ether layer was dried over anhydrous magnesium sulfate and filtered. By distilling off the solvent, N-t-butyldimethylsilyloxycarbonylthreonine methyl ester was obtained in an amount of 215 mg (yield, 99%).

Appearance: colorless oil.
IR spectrum (film, cm$^{-1}$): 3460, 1758, 1706, 1518.
Mass spectrum (m/z): 276 (M$^+$—CH$_3$), 247, 234, 215.
NMR spectrum (CDCl$_3$, δ ppm): 5.60(1H, d, J=9.0 Hz), 4.20(2H, m), 3.70(3H, s), 3.15(1H, brs), 1.20(3H, d, J=7.0 Hz), 0.92(9H, s), 0.25(6H, s).

EXAMPLE 14

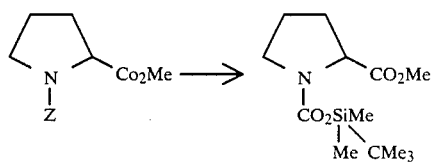

To a dichloromethane solution (1.0 ml) of palladium (II) acetate (9.0 mg, 0.04 mmol) and triethylamine (17 μl, 0.12 mmol), t-butyldimethylsilane (199 μl, 1.2 mmol) was added and the mixture was stirred for 15 minutes at room temperature in an argon atmosphere. To the resulting black suspension, a dichloromethane solution (1.0 ml) of Z-proline methyl ester (210 mg, 0.80 mmol) was added and the mixture was stirred for an additional 15 hours. After a saturated aqueous solution of ammonium chloride was added to quench the reaction, extraction with ether was conducted and the ether layer was dried over anhydrous magnesium sulfate and filtered. By distilling off the solvent, N-t-butyldimethylsilyloxycarbonylproline methyl ester was obtained in an amount of 230 mg (yield, 100%). The physical data for this compound were in agreement with those reported in Example 7.

REFERENCE EXAMPLE 1

N-(Benzyloxycarbonyl)-2-amino-4-pentenoyl-threonine methyl ester

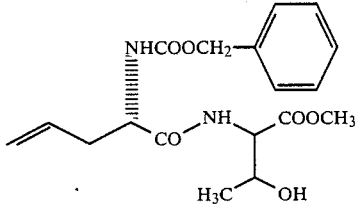

To a tetrahydrofuran solution (1.0 ml) of the compound prepared in Example 1 (43.3 mg, 0.07 mmol), were added at 0° C. in a nitrogen atmosphere benzyl bromide (0.025 ml, 0.21 mmol) and a tetrahydrofuran solution of tetrabutylammonium fluoride (0.14 ml, 0.14 mmol) were successively added dropwise. The mixture was stirred for 1 hour at 0° C., poured into water and extracted with ether. The ether layer was dried over anhydrous magnesium sulfate and concentrated under vacuum. The resulting reaction mixture was subjected to column chromatography (ether/hexane=3/1) to give 14.3 mg of the titled compound (total yield from Example 1, 54%).

Appearance: colorless needle (recrystallized from ether).

m.p.: 106°–106.5° C.

IR spectrum (CHCl$_3$, cm$^{-1}$): 3440, 1730, 1686, 1504.

Mass spectrum (m/z): 364 (M$^+$), 320.

NMR spectrum (CDCl$_3$, δ): 1.15(3H, d, J=7 Hz), 2.52(2H, m), 2.92(1H, brs), 3.72(3H, s), 4.0–6.0(9H) 5.08(2H, s), 6.96(1H, d, J=8 Hz), 7.32(5H, s).

REFERENCE EXAMPLE 2

N-(Benzyloxycarbonyl)-2-amino-4-pentenoyl-O-(tetrahydropyranyl)-threonine metal ester

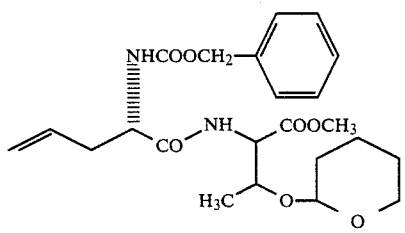

To a tetrahydrofuran solution (1.0 ml) of the compound prepared in Example 2 (45.8 mg, 0.09 mmol), were successively added dropwise at 0° C. in a nitrogen atmosphere benzyl bromide (0.021 ml, 0.18 mmol) and a tetrahydrofuran solution of tetrabutyl ammonium fluoride (0.090 ml, 0.09 mmol). The mixture was stirred for 1 hour at 0° C., poured into water and extracted with ether. The ether layer was dried over anhydrous magnesium sulfate and the solvent was distilled off under vacuum. The resulting reaction mixture was subjected to column chromatography (ether/hexane=1/1) to give 31.2 mg of the titled compound (yield, 78% based on the starting materials used in Example 2).

Appearance: colorless oil.

IR spectrum (CHCl$_3$, cm$^{-1}$): 3450, 2960, 1748, 1726, 1684, 1504.

Mass spectrum (m/z): 448 (M$^+$), 407, 320.

NMR spectrum (CDCl$_3$, δ): 1.14 and 1.24 (3H in all, d each, J=7.0 Hz), 1.32–1.90(6H, m), 2.56(2H, m), 3.72(3H, s), 5.10(2H, s), 7.34(5H, s).

REFERENCE EXAMPLE 3

Methyl N-methoxycarbonyl-2-amino-4-pentenoate

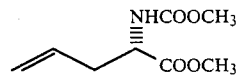

To a tetrahydrofuran solution (3.0 ml) of the compound prepared in Example 3 (170 mg, 0.59 mmol), were successively added dropwise at 0° C. in a nitrogen atmosphere methyl iodide (0.074 ml, 1.18 mmol) and a tetrahydrofuran solution of tetrabutylammonium fluoride (0.59 ml, 0.59 mmol). The mixture was agitated for 1 hour at 0° C., poured into water and extracted with ether. The ether layer was dried over anhydrous magnesium sulfate and the solvent was distilled off under vacuum. The resulting reaction mixture was subjected to column chromatography and eluted with a 1:4 mixture of ether and hexane to give 93 mg of the titled compound (yield, 84% based on the starting materials used in Example 3).

Appearance: colorless oil.

IR spectrum (CHCl$_3$, cm$^{-1}$): 3456, 3020, 1726, 1512.

Mass spectrum (m/z): 188 (M+1)$^+$, 128.

NMR spectrum (CDCl$_3$, δ): 2.52(2H, m), 3.68(3H, s), 3.75(3H, s), 4.40(1H, dt, J=8, 7 Hz), 4.8–6.0(4H, m).

REFERENCE EXAMPLE 4

Methyl N-(2-propenyloxycarbonyl)-2-amino-4-pentenoate

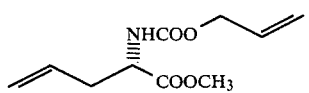

To a tetrahydrofuran solution (3.0 ml) of the compound prepared in Example 3 (170 mg), were successively added dropwise at 0° C. in a nitrogen atmosphere allyl bromide (0.086 ml, 0.99 mmol) and a tetrahydrofuran solution of tetrabutylammonium fluoride (0.49 ml, 0.49 mmol). After the mixture was stirred for 1 hour at 0° C., it was treated as in Reference Example 3 to give the titled compound in an amount of 86 mg (yield, 82% based on the starting materials used in Example 3).

Appearance: colorless oil.

IR spectrum (film, cm$^{-1}$): 3352, 3100, 2960, 1732, 1648, 1532.

Mass spectrum (m/z): 214 (M+1)$^+$, 173, 155.

NMR spectrum (CDCl$_3$, δ): 2.53(2H, brt, J=7 Hz), 3.71(3H, s), 4.0–4.7(3H, m), 4.9–6.3(7H, m).

REFERENCE EXAMPLE 5

Methyl N-(benzyloxycarbonyl)-2-amino-4-pentenoate

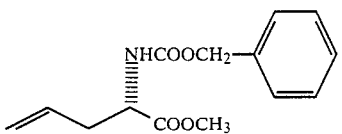

To a tetrahydrofuran solution (1.0 ml) of the compound prepared in Example 3 (185 mg, 0.57 mmol), were successively added dropwise at 0° C. in a nitrogen atmosphere benzyl bromide (0.135 ml, 1.14 mmol) and a tetrahydrofuran solution of tetrabutyl ammonium fluoride (0.57 ml, 0.57 mmol). The mixture was stirred for 1 hour at 0° C., it was treated as in Reference Example 3 to give the titled compound in an amount of 131.2 mg (yield, 88% based on the starting materials used in Example 3).

Appearance: colorless oil.
IR spectrum (film, cm$^{-1}$): 3356, 1730, 1646, 1530.
Mass spectrum (m/z): 263 (M)$^+$, 222, 204.
NMR spectrum (CDCl$_3$, δ): 2.55(2H, brt, J=7 Hz), 3.72(3H, s), 4.48(1H, dt, J=8, 7 Hz), 5.09(2H, s), 4.8–6.0(4H, m), 7.32(5H. s).

REFERENCE EXAMPLE 6

N-(Benzyloxycarbonyl)-valine methyl ester

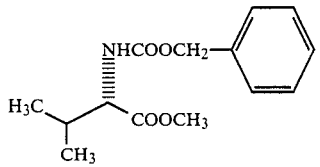

To a tetrahydrofuran solution (1.0 ml) of the compound prepared in Example 4 (130 mg, 0.42 mmol), were successively added dropwise at 0° C. in a nitrogen atmosphere benzyl bromide (0.101 ml, 0.84 mmol) and a tetrahydrofuran solution of tetrabutyl ammonium fluoride (0.42 ml, 0.42 mmol). The mixture was stirred for 1 hour at 0° C., poured into water and extracted with ether. The ether layer was dried over anhydrous magnesium sulfate and concentrated under vacuum. The resulting reaction mixture was subjected to column chromatography on silica gel and eluted with a 1:4 mixture of ether and hexane, to give the titled compound in an amount of 95.1 mg (yield, 85% based on the starting materials used in Example 4).

Appearance: colorless oil.
IR spectrum (film, cm$^{-1}$): 3360, 1728, 1522.
Mass spectrum (m/z): 265 (M)$^+$, 222, 207.
NMR spectrum (CDCl$_3$, δ): 0.90(3H, d, J=7.0 Hz), 0.96(3H, d, J=7.0 Hz), 2.05 (1H, m), 3.68(3H, s), 4.27(1H, m), 5.07(2H, s), 5.45(1H, d, J=9 Hz), 7.30(5H, s)

$[\alpha]_D^{30}$: −19.4° (C=1.0 in MeOH).
Documented $[\alpha]_D^{20}$: −21.9° (C=1.0 in MeOH).

REFERENCE EXAMPLE 7

N-Benzyloxycarbonyl-L-methionine methyl ester

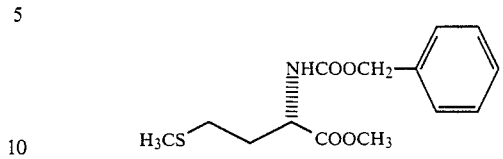

To a tetrahydrofuran solution (1 ml) of the compound prepared in Example 5 (146 mg, 0.45 mmol), were successively added dropwise at 0° C. under a nitrogen stream benzyl bromide (0.06 ml, 0.5 mmol) and a tetrahydrofuran solution of tetrabutyl ammonium fluoride (0.45 ml, 0.45 mmol). After the mixture was stirred for 1 hour at 0° C., it was treated as in Reference Example 6 and eluted with a 3:7 mixture of ether and hexane to give the titled compound in an amount of 91.2 mg (yield, 61% based on the starting materials used in Example 5).

Appearance: colorless oil.
IR spectrum (film, cm$^{-1}$): 3348, 1726, 1532.
Mass spectrum (m/z): 297 (M+), 238, 223, 162, 145.
NMR spectrum (CDCl$_3$, δ): 2.08(3H, s), 1.7–2.7(4H, m), 3.72(3H, s), 4.50(1H, m), 5.09(2H, s), 7.31(5H, s).
$[\alpha]_D^{20}$: −32.6° (C=1.0 in MeOH).
Documented $[\alpha]_D^{20}$: −35.6° (C=1.0 in MeOH).

REFERENCE EXAMPLE 8

N-(Benzyloxycarbonyl)-L-phenylalanine methyl ester

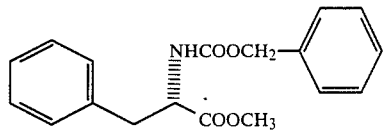

To a tetrahydrofuran solution (1 ml) of the compound prepared in Example 6 (174 mg, 0.5 mmol), were succcessively added dropwise at 0° C. in a nitrogen atmosphere benzyl bromide (0.119 ml, 1.0 mmol) and a tetrahydrofuran solution of tetrabutyl ammonium fluoride (0.5 ml, 0.5 mmol). After the mixture was stirred for 1 hour at 0° C., it was poured into water and extracted with ether. The ether layer was dried over anhydrous magnesium sulfate and concentrated under vacuum. The resulting reaction mixture was subjected to column chromatography on silica gel and eluted with a 3:7 mixture of ether and hexane to give the titled compound in an amount of 122 mg (yield, 78% based on the starting materials used in Example 6)

Appearance: colorless oil.
IR spectrum (film, cm$^{-1}$): 3356, 3036, 2960, 1726, 1518.
Mass spectrum (m/z): 313 (M+), 254.
NMR spectrum (CDCl$_3$, δ): 3.07(2H, d, J=6.0 Hz), 3.65(3H, s), 4.63(1H, dt, J=8.0, 6.0 Hz), 5.05(2H, s), 5.30(1H, d, J=8.0 Hz), 7.28(5H, s), 6.9–7.3(5H, m).
$[\alpha]_D^{30}$: −14.9° (C=1.0 in MeOH).
Documented $[\alpha]_D^{20}$: −17.1° (C=1.0 in MeOH).

REFERENCE EXAMPLE 9

L-Phenylalanine methyl ester

To a tetrahydrofuran solution (1.0 ml) of the compound prepared in Example 6 (187 mg, 0.5 mmol), were successively added dropwise at room temperature water (0.5 ml) and a tetrahydrofuran solution of tetrabutyl ammonium fluoride (0.5 ml, 0.5 mmol). After the mixture was stirred for 15 minutes at room temperature, it was extracted with ether and the ether layer was dried over anhydrous magnesium sulfate and concentrated under vacuum. The resulting reaction mixture was subjected to column chromatography and eluted with a mixture of ether and ethyl acetate, to give the titled compound in an amount of 84 mg (yield, 93% based on the starting materials used in Example 6).

Appearance: colorless oil.

Mass spectrum (m/z): 180 (M+1)$^{30}$, 120, 91.

NMR spectrum (60 MHz, CDCl$_3$, δ): 1.57(2H, s), 2.80(1H, dd, J=15.0, 6.0 Hz), 3.12(1H, dd, J=15.0, 8.0 Hz), 3.68(3H, s), 3.70(1H, dd, J=8.0, 6.0 Hz), 7.20(5H, s).

The obtained L-phenylalanine methyl ester was dissolved in ether, mixed with HCl-gas saturated ether and treated by routine procedures to form a hydrochloride form of said ester.

Appearance: colorless needle.

m.p.: 157°–160.5° C. (documented value: 158°–162° C.).

REFERENCE EXAMPLE 10

N-(Benzyloxycarbonyl)-L-proline methyl ester

To a tetrahydrofuran solution (1 ml) of the compound prepared in Example 7 (146 mg), were successively added dropwise at 0° C. in a nitrogen atmosphere benzyl bromide (0.114 ml, 0.96 mmol) and a tetrahydrofuran solution of tetrabutyl ammonium fluoride (0.48 ml, 0.48 mmol). The mixture was stirred for 1 hour at 0° C., poured into water and extracted with ether. The ether layer was dried over anhydrous magnesium sulfate and concentrated under vacuum. The resulting reaction mixture was subjected to column chromatography on silica gel and eluted with a 1:1 mixture of ether and hexane to give the titled compound in an amount of 94 mg (yield, 75% based on the starting materials used in Example 7).

Appearance: colorless oil.

IR spectrum (film, cm$^{-1}$): 2960, 2888, 1750, 1708.

Mass spectrum (m/z): 263 (M$^+$), 204, 160.

NMR spectrum (CDCl$_3$, δ): 1.6–2.4(4H, m), 3.3–3.8(5H, m), 4.40(1H, m), 5.12(2H, s), 7.30(5H, s).

$[\alpha]_D^{30}$: −62.0° (C=1.0 in MeOH).

Documented $[\alpha]_D^{20}$: −64.0° (C=1.0 in MeOH).

REFERENCE EXAMPLE 11

Benzyl (4S*,5R*,6R*)-N-(benzyloxycarbonyl)-5-amino-2,2-dimethyl-6-vinyl-1,3-dioxane-4-acetate To a tetrahydrofuran solution (1.0 ml) of the compound obtained in Example 8 (43 mg, 0.1 mmol), were successively added dropwise at 0° C. in a nitrogen atmosphere benzyl bromide (0.024 ml, 0.2 mmol) and a tetrahydrofuran solution of tetrabutyl ammonium fluoride (0.15 ml, 0.15 mmol). After the mixture was stirred for 1 hour at 0° C., it was poured into water and extracted with ether. The ether layer was dried over anhydrous magnesium sulfate and the solvent was distilled off under vacuum. The resulting reaction mixture was subjected to column chromatography on silica gel and eluted with a 1:4 mixture of ether and hexane to give the titled compound in an amount of 30 mg (yield, 73% based on the starting materials used in Example 8).

Appearance: colorless prism (recrystallized from hexane).

m.p.: 39.0°–40.8° C.

IR spectrum (film, cm$^{-1}$): 3450, 1732.

Mass spectrum (m/z): 406 (M+1)$^+$, 390, 291.

NMR spectrum (CDCl$_3$, δ): 1.40(3H, s), 1.44(9H, s), 1.50(3H, s), 2.20(2H, d, J=7 Hz), 3.69(1H, ddd, J=11, 2.0, 2.0 Hz), 4.2–4.6(2H, m), 5.08(2H, s), 5.0–6.0(4H, m), 7.34(5H, s).

The present invention offers an economical and efficient method for providing compounds useful as intermediates for the production of a variety of carbamate esters that can be extensively used as drugs acting on the central nervous system or circulatory organs, as agrichemicals (e.g. insecticides, acaricides and herbicides), or as antimicrobial agents. Therefore, the present invention will offer great benefit to industry, especially in medical and related fields.

What is claimed is:

1. A process for producing a t-butyldimethylsilyl carbamate derivative of the general formula (1):

$$\begin{array}{c} R^1 \\ \diagdown \\ \diagup \\ R^2 \end{array} N-COO-\underset{\underset{CH_3}{|}}{\overset{\overset{CH_3}{|}}{Si}}-C(CH_3)_3 \qquad (1)$$

where R$^1$ is an alkyl group having 1–3 carbon atoms or a hydrogen atom; R$^2$ is $$-CH\begin{array}{c} \diagup R^3 \\ \diagdown R^4 \end{array}$$

(where R$^3$ is a hydrogen atom, an alkyl, alkenyl or aralkyl group having 1–10 carbon atoms, each of which groups may be substituted by a hydroxyl group, a t-butyldimethylsilyloxy group, a methylthio group, a lower alkoxycarbonyl group, a lower alkoxy group, an indolyl group or an imidazolyl group; $R^4$ is a lower alkoxycarbonyl group, an N-alkylamido group having 2-6 carbon atoms, an O-tetrahydropyranylthreonine methyl ester amido residue, an O-t-butyldimethylsilyl-threonine methyl ester amido residue, a threonine methyl ester amido residue or $-(CH_2)_n-COOR^5$ (where n is an integer of 1-3 and $R^5$ is a lower alkyl group), provided that $R^3$ combines with $R^4$ to form a cyclopentyl group, a cyclohexyl group, a tetrahydrofuranyl group or a dioxanyl group, these rings being optionally substituted by a lower alkyl group, a lower alkenyl group, a lower alkoxycarbonyl group or a lower alkoxycarbonylmethyl group); and $R^1$ and $R^2$, when taken together, form a 4- or 5-membered carbon ring, which may be substituted by a lower alkoxycarbonyl group or a t-butyldimethylsilyloxycarbonyl group, said process comprising treating a t-butyl carbamate derivative of the formula (2):

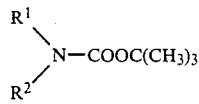
(2)

(where $R^1$ and $R^2$ are the same as defined above) with t-butyldimethylsilyl trifluoromethane sulfonate (TBDMSOTf) of the formula:

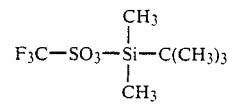

in the presence of a base, or reacting a carbamate derivative of the formula (3):

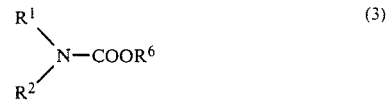
(3)

(where $R^1$ and $R^2$ are the same as defined above; $R^6$ is an allyl or benzyl group) with t-butyldimethylsilane of the formula:

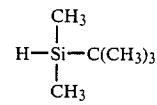

in the presence of a palladium catalyst.

2. A process according to claim 1 wherein said base is lutidine, dimethylaminopyridine, triethylamine, diisopropylethylamine, pyridine or triisopropylamine.

3. A process according to claim 1 wherein said palladium catalyst is palladium on carbon, palladium (II) chloride, palladium (II) acetate, dichlorobis(acetonitrile) palladium (II) or dichlorobis(triphenylphosphine) palladium (II).

* * * * *